(12) United States Patent
Homyk et al.

(10) Patent No.: US 9,018,684 B2
(45) Date of Patent: Apr. 28, 2015

(54) CHEMICAL SENSING AND/OR MEASURING DEVICES AND METHODS

(75) Inventors: Andrew P. Homyk, South Pasadena, CA (US); Michael D. Henry, Albuquerque, NM (US); Axel Scherer, Woodstock, VT (US); Sameer Walavalkar, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 365 days.

(21) Appl. No.: 12/952,181

(22) Filed: Nov. 22, 2010

(65) Prior Publication Data

US 2012/0161207 A1 Jun. 28, 2012

Related U.S. Application Data

(60) Provisional application No. 61/263,702, filed on Nov. 23, 2009.

(51) Int. Cl.
| | | |
|---|---|---|
| *H01L 29/772* | (2006.01) | |
| *H01L 29/02* | (2006.01) | |
| *H01L 29/06* | (2006.01) | |
| *B82Y 10/00* | (2011.01) | |
| *H01L 29/775* | (2006.01) | |
| *G01N 27/414* | (2006.01) | |
| *B82Y 15/00* | (2011.01) | |

(52) U.S. Cl.
CPC ............ *H01L 29/0676* (2013.01); *B82Y 10/00* (2013.01); *B82Y 15/00* (2013.01); *H01L 29/775* (2013.01); *G01N 27/4146* (2013.01)

(58) Field of Classification Search
CPC ............................. H01L 29/02; H01L 29/772
USPC .......... 436/149, 150, 151; 257/253, 288, 618, 257/E29.242, E29.002, E21.409; 438/49
See application file for complete search history.

(56) References Cited

U.S. PATENT DOCUMENTS

| | | |
|---|---|---|
| 4,322,571 A | 3/1982 | Stanbery |
| 6,586,787 B1 | 7/2003 | Shih et al. |
| 6,593,065 B2 | 7/2003 | Scherer |
| 6,831,017 B1 | 12/2004 | Li et al. |
| 7,302,146 B2 | 11/2007 | Turner et al. |
| 7,419,908 B2 | 9/2008 | Green |

(Continued)

FOREIGN PATENT DOCUMENTS

| | | |
|---|---|---|
| JP | 2004-193525 | 2/2007 |
| JP | 2007-194646 | 2/2007 |

(Continued)

OTHER PUBLICATIONS

PCT International Search Report issued for PCT Application No. PCT/US2010/025256 filed on Feb. 24, 2010 in the name of California Institute of Technology et al.

(Continued)

*Primary Examiner* — Kevin Parendo
*Assistant Examiner* — Lamont Koo
(74) *Attorney, Agent, or Firm* — Steinfl & Bruno, LLP

(57) ABSTRACT

Methods for fabricating silicon nanowire chemical sensing devices, devices thus obtained, and methods for utilizing devices for sensing and measuring chemical concentration of selected species in a fluid are described. Devices may comprise a metal-oxide-semiconductor field-effect transistor (MOSFET) structure.

13 Claims, 4 Drawing Sheets

(56) References Cited

U.S. PATENT DOCUMENTS

| | | | |
|---|---|---|---|
| 7,947,430 | B2 | 5/2011 | Fu et al. |
| 8,067,763 | B2 | 11/2011 | Wang et al. |
| 2002/0127495 | A1 | 9/2002 | Scherer |
| 2004/0071951 | A1 | 4/2004 | Jin |
| 2004/0108298 | A1 | 6/2004 | Gao |
| 2005/0279989 | A1 | 12/2005 | Li et al. |
| 2006/0063368 | A1 | 3/2006 | Sharma |
| 2006/0088995 | A1 | 4/2006 | Zhang et al. |
| 2006/0118975 | A1 | 6/2006 | Koenenkamp |
| 2006/0131695 | A1 | 6/2006 | Kuekes et al. |
| 2006/0207647 | A1 | 9/2006 | Tsakalakos et al. |
| 2007/0126079 | A1* | 6/2007 | Shioya et al. ............... 257/532 |
| 2007/0132043 | A1* | 6/2007 | Bradley et al. ............... 257/414 |
| 2008/0009121 | A1 | 1/2008 | Wei |
| 2008/0035983 | A1 | 2/2008 | Sandhu et al. |
| 2008/0036038 | A1 | 2/2008 | Hersee et al. |
| 2008/0092938 | A1 | 4/2008 | Majumdar et al. |
| 2008/0102319 | A1 | 5/2008 | Bratkovski et al. |
| 2008/0142970 | A1 | 6/2008 | Evans et al. |
| 2008/0149944 | A1 | 6/2008 | Samuelson et al. |
| 2008/0156369 | A1 | 7/2008 | Ko et al. |
| 2008/0203431 | A1* | 8/2008 | Garcia et al. ............... 257/192 |
| 2008/0211040 | A1* | 9/2008 | Lieber et al. ............... 257/414 |
| 2008/0230802 | A1 | 9/2008 | Bakkers et al. |
| 2009/0203214 | A1 | 8/2009 | Hurkx et al. |
| 2010/0006817 | A1 | 1/2010 | Ohlsson et al. |
| 2010/0019355 | A1 | 1/2010 | Kamins et al. |
| 2010/0033561 | A1 | 2/2010 | Hersee |
| 2010/0068828 | A1 | 3/2010 | Thomas et al. |
| 2010/0176822 | A1* | 7/2010 | Offermans et al. ........... 324/663 |
| 2010/0213579 | A1 | 8/2010 | Henry et al. |
| 2010/0215543 | A1 | 8/2010 | Henry et al. |
| 2010/0291385 | A1 | 11/2010 | Greer et al. |
| 2011/0031470 | A1 | 2/2011 | Scherer et al. |
| 2011/0165724 | A1 | 7/2011 | Guha et al. |

FOREIGN PATENT DOCUMENTS

| | | |
|---|---|---|
| JP | 2008130712 | 5/2008 |
| WO | 00/21118 | 8/2000 |
| WO | 2005/076381 | 8/2005 |
| WO | 2007/077842 | 7/2007 |
| WO | 2008/129478 | 10/2008 |
| WO | 2010/099216 | 9/2010 |
| WO | 2010/099220 | 9/2010 |
| WO | 2010/151604 | 12/2010 |

OTHER PUBLICATIONS

PCT International Search Report issued for PCT Application No. PCT/US2010/025261 filed on Feb. 24, 2010 in the name of California Institute of Technology et al.

PCT Written Opinion issued for PCT Application No. PCT/US2010/025256 filed on Feb. 24, 2010 in the name of California Institute of Technology et al.

PCT Written Opinion issued for PCT Application No. PCT/US2010/025261 filed on Feb. 24, 2010 in the name of California Institute of Technology et al.

Bogglid, P., et al., Fabrication and Actuation of Customized Nanotweezers with a 25 nm Gap, Nanotechnology 2001, 12: 331-335.

Chang, Y.F., et al., Fabrication of High-aspect-ratio Silicon Nanopillar Arrays with the Conventional Reactive Ion Etching Technique, Applied Physics A 2007, 86: 193-196.

de Boer, M., et al., Guidelines for Etching Silicon MEMS Structures Using Flourine High-density Plasmas at Cryogenic Temperatures, Journal of Microelectromechanical Systems 2002, 11: 385-401.

Hashemi, P., et al., Asymmetric Strain in Nanoscale Patterned Strained-Si/strained-Ge/strained-Si Heterostructures on Insulator, Applied Physics Letters 2007, 91: 083109-1 083109-3.

Hon, K., et al., Periodically Poled Silicon, Applied Physics Letters 2009, 94: 091116-1 091116-3.

Jacobsen, R., et al., Strained Silicon as a New Electro-optic Material, Nature 2006, 441: 199-202.

Kayes, B.M., et al., Comparison of the Device Physics Principles of p-n Junction Nanorod Solar Cells, Journal of Applied Physics 2005, 97: 114302-1 114302-11.

Kelzenberg, M.D., et al., Single-nanowire Si Solar Cells, Nanotechnology Letters 2008, 8: 710-714.

Lauhon, L., et al., Epitaxial Core-shell and Core-multishell Nanowire Heterostructures, Nature 2002, 420: 57-61.

Moser, B., et al., Strength and Fracture of Si Micropillars: A new scanning electron microscopy-based micro-compression test, Journal of Material Resources 2007, 22: 1004-1011.

Nassiopoulos, A., et al., Electroluminescent Device Based on Silicon Nanopillars, Applied Physics Letters 1996, 69: 2267-2269.

Photopoulos, P., et al. Photoluminescence from Nanocrystalline Silicon in Si/SiO2 Superlattices, Applied Physics Letters 2000, 76: 3588-3590.

Rangelow, I.W., et al., Critical Tasks in High Aspect Ratio Silicon Dry Etching for Microelectromechanical Systems, Journal of Vaccum Science Technology A 2003, 21: 1150-1562.

Sainiemi, L., et al., Rapid Fabrication of High Aspect Ratio Silicon Nanopillars for Chemical Analysis, Nanotechnology 2007, 18: 505303-1 505303-7.

Sainiemi, L., et al., Mask Material Effects in Cryogenic Deep Reactive Ion Etching, Journal of Vacuum Science Technology B 2007, 25: 801-807.

Sajjad, R., et al., Electronic Properties of a Strained <100> Silicon Nanowire, Journal of Applied Physics 2009, 105: 044307-1 044307-6.

Scheible, D., et al., Silicon Nanopillars for Mechanical Single-electron Transport, Applied Physics Letters 2004, 84: 4632-4634.

Singh, J., Electronic and Optoelectronic Properties of Semiconductor Structures, In Electronic and Optoelectronic Properties of Semiconductor Structures, 2003, Cambridge University Press, Chapter 1.4 Strained heterostructures, 26-31.

Singh, N., et al., High-Performance Fully Depleted Silicon Nanowire (Diameter ≤ 5 nm) Gate-All-Around CMOS Devices, IEEE Electron Device Letters 2006, 27:383-386.

Tang, Z., et al., Finite Temperature Quasicontinuum Method for Multiscale Analysis of Silicon Nanostructures, Physical Review 2006, 74: 064100-1 061400-16.

Teh, W., et al., Cross-linked PMMA as a low Dimensional Sacrificial Layer, Journal of Electromechanical Systems 2003, 12: 641-648.

Timoshenko, S., Analysis of Bi-metal Thermostats, Journal of the Optical Society of America 1925, 11: 233-255.

Welch, C.C., et al., Silicon Etch Process Options for Micro-and Nanotechnology Using Inductively Coupled Plasmas, Microelectronic Engineering 2006, 83: 1170-1173.

Williams, K.R., et al., Etch Rates for Micromachining Processing Part, Journal of Microelectromechanical Systems 2003, 12: 761-778.

Yeom, J., et al., Maximum Achievable Aspect Ratio in Deep Reactive Ion Etching of Silicon due to Aspect Ratio Dependent Transport and the Microloading Effect, Journal of Vacuum Science Technology 2005, 23: 2319-2329.

Zailer, I., et al., Crosslinked PMMA as a High-resolution Negative Resist for Elctron Beam Lithography and Applications for Physics of lowdimensional Structures, Semiconductor Sci. Technol. 1996, 11: 1235-1238.

Ambrose, D., et al., Vapour pressures up to their critical temperatures of normal alkanes and 1-alkanois, Pure & Applied Chemistry 1989, 61: 1395-1403.

Cassie, A., et al., Wettability of porous surfaces, Transactions of the Faraday Society 1944, 40: 546-551.

Chirico, R., et al., Vapor pressure on-Alkanes revisted. New high-precision vapor pressure data on n-Decane, n-Elcosane, and n-Octacosane, J. Chem. Eng. Data 1989, 34: 149-156.

Ebron, V., et al., Fuel-powered artificial muscles, Science 2006, 311: 1580-1584.

Gao, L., et al., The "lotus effect" explained: Two reasons why two length scales of topography are important, Langmuir 2006, 22: 2966-2967.

(56) References Cited

OTHER PUBLICATIONS

Henry, M., et al., Alumina etch masks for fabrication of high-aspect-ratio silicon micropillars and naopillars, Nanotechnology 2009, 20: 255305-1-255305-4.
Kim, H., et al., Field emission from a single nanomechanical pillar, Nanotechnology 2007, 18: 065201-1-065201-4.
Kuan, W., et al., The preparation of superhydrophobic surfaces of hierarchical silicon nanotube structures, Nanotechnology 2009, 20: 035605-1-035605-8.
Li, H., et al., Investigation of capacitive humidity sensing behavior of silicon nanowires, Physica E 2009, 41: 600-604.
Wiener, H., Vapor pressure-temperature relationships among the branched paraffin hydrocarbons, ACS 1948, 425-430.
Oxford Plasma Technology Applications Engineering Group "Plasmalab" Process Data Sheet, 'Bosch' Silicon Etch Process, 'Cryo' Silicon Etch Process, and Silicon Etch Process.
Advisory Action mailed on Dec. 6, 2012 for U.S. Appl. No. 13/712,097, filed Feb. 24, 2010 in the name of Michael D. Henry et al.
Advisory Action mailed on Nov. 2, 2012 for U.S. Appl. No. 13/712,097, filed Feb. 24, 2010 in the name of Michael D. Henry et al.
Final Office Action mailed on Jul. 30, 2012 for U.S. Appl. No. 13/712,097, filed Feb. 24, 2010 in the name of Michael D. Henry et al.
Final Office Action mailed on Mar. 4, 2013 for U.S. Appl. No. 12/949,758, filed Nov. 18, 2010 in the name of Andrew P. Homyk et al.
PCT International Preliminary on Patentability (IPRP) mailed on Oct. 20, 2010 for PCT application PCT/US2010/025261 filed on Feb. 24, 2010 in the name of California Institute of Technology et al.
PCT International Search Report (ISR) mailed on Jun. 24, 2011 for PCT application PCT/US2010/057301 filed on Nov. 18, 2010 in the name of California Institute of Technology et al.
PCT Written Opinion mailed on Jun. 24, 2011 for PCT application PCT/US2010/057301 filed on Nov. 18, 2010 in the name of California Institute of Technology et al.
Non-Final Office Action mailed on Oct. 7, 2011 for U.S. Appl. No. 12/712,097, filed Feb. 24, 2010 in the name of Michael D. Henry et al.
Non-Final Office Action mailed on Oct. 17, 2011 for U.S. Appl. No. 12/711,992, filed Feb. 24, 2010 in the name of Michael D. Henry et al.
Non-Final Office Action mailed on Sep. 19, 2012 for U.S. Appl. No. 12/949,758, filed Nov. 18, 2010 in the name of Andrew P. Homyk et al.
Notice of Allowance mailed on Sep. 12, 2011 for U.S. Appl. No. 12/822,109, filed Jun. 23, 2010 in the name of Axel Scherer et al.
Notice of Allowance mailed on May 23, 2011 for U.S. Appl. No. 12/822,109, filed Jun. 23, 2010 in the name of Axel Scherer et al.
Notice of Allowance mailed on Jan. 27, 2012 for U.S. Appl. No. 12/711,992, filed Feb. 24, 2010 in the name of Michael D. Henry et al.
Restriction Requirement mailed on Mar. 30, 2011 for U.S. Appl. No. 12/822,109, filed Jun. 23, 2010 in the name of Axel Scherer et al.
Restriction Requirement mailed on Jul. 13, 2011 for U.S. Appl. No. 12/712,097, filed Feb. 24, 2010 in the name of Michael D. Henry et al.
Restriction Requirement mailed on May 1, 2012 for U.S. Appl. No. 12/712,097, filed Feb. 24, 2010 in the name of Michael D. Henry et al.
Restriction Requirement mailed on Aug. 29, 2012 for U.S. Appl. No. 12/949,758, filed Nov. 18, 2010 in the name of Andrew P. Homyk et al.
Non-Final Office Action mailed on Jun. 19, 2013 issued for U.S. Appl. No. 12/949,758, filed Nov. 18, 2010 in the name Andrew P. Homyk et al.
European Search Report mailed on Jun. 2, 2014 for EP 10792619.8 filed on Dec. 15, 2011 in the name of California Institute of Technology.
International Search Report mailed on Feb. 24, 2011 for PCT/US2010/039702 filed on Jun. 23, 2010 in the name of California Institute of Technology, et al.
Written Opinion mailed on Feb. 24, 2011 for PCT/US2010/039702 filed on Jun. 23, 2010 in the name of California Institute of Technology.
Non-Final Office Action mailed on May 7, 2013 for U.S. Appl. No. 13/286,008, filed Oct. 31, 2011 in the name of California Institute of Technology.
Non-Final Office Action mailed on Jun. 19, 2013 for U.S. Appl. No. 12/949,758, filed Nov. 18, 2010 in the name of California Institute of Technology.
Final Office Action mailed on Oct. 17, 2013 for U.S. Appl. No. 12/949,758, filed Nov. 18, 2010 in the name of California Institute of Technology.
Notice of Allowance mailed on May 20, 2014 for U.S. Appl. No. 12/949,758, filed Nov. 18, 2010 in the name of California Institute of Technology.
Chang, Y-F et al. "Fabrication of high-aspect-ratio silicon nanopillar arrays with the conventional reactive ion etching technique" *Applied Physics A* 86, 193-196 (2007).
Chen, M-H, et al. "Self-masked high-aspect-ratio polymer nanopillars" *Nanotechnology* 19 (2008) 505301 1-7.

\* cited by examiner

US 9,018,684 B2

CHEMICAL SENSING AND/OR MEASURING DEVICES AND METHODS

CROSS REFERENCE TO RELATED APPLICATIONS

The present application claims priority to U.S. Provisional Application No. 61/263,702, filed on Nov. 23, 2009 which is incorporated herein by reference in its entirety. The present application may be related to U.S. patent application Ser. No. 12/712,097 for 'Methods for Fabricating High Aspect Ratio Probes and Deforming High Aspect Ratio Nanopillars and Micropillars' filed on Feb. 24, 2010, U.S. patent application Ser. No. 12/711,992 for 'Methods for Fabrication of High Aspect Ratio Micropillars and Nanopillars' filed on Feb. 24, 2010, and U.S. patent application Ser. No. 12/822,109 for "Methods for Fabricating Passivated Silicon Nanowires and Devices Thus Obtained," filed on Jun. 23, 2010, the disclosures of all of which are also incorporated herein by reference in their entirety.

STATEMENT OF GOVERNMENT GRANT

This invention was made with government support under Grant No. HR0011-04-1-0054 awarded by the DARPA, Grant No. FA9550-04-1-0434 awarded by the AFOSR and Grant No. W911NF-07-1-0277 awarded by the ARO. The government has certain rights in the invention.

FIELD

The present disclosure relates to silicon nanowire methods and/or devices. Moreover in particular, it relates to chemical sensing and/or measuring devices and methods.

BACKGROUND

Defining high aspect ratio structures with controllable sidewalls in silicon has become increasingly important both in the nanometer and micrometer scale for solar cells, microelectronic devices, and chemical analysis. High aspect ratio micrometer pillars can be used for solar cell investigations while nanometer scale high aspect ratio pillars can enable fundamental investigations in theories of nanopillar stress mechanics, silicon based lasers, and nanoscale electronic devices such as finFETs and chemical sensors. Currently various nanofabrication techniques exist that rely on self assembly or bottom-up processing. Some top-down processing enabling reproducibility in nanofabrication can also be found.

Among further possible applications are mechanical oscillators and piezo-resistive sensors. High aspect ratio nanopillars with diameters between 50-100 nm could prove useful for core-shell type plasmonic resonators while nanopillars with sub-10 nm diameters have shown promising light emission characteristics.

SUMMARY

According to a first aspect, a device is provided, comprising: a semiconductor substrate with a planar surface; a semiconductor nanopillar on the semiconductor substrate and substantially perpendicular to the planar surface; an insulating layer covering the semiconductor nanopillar; a conductive layer covering the insulating layer, wherein the conductive layer and the insulating layer are devoid of an end portion thereof, thus exposing an uninsulated pillar end of the semiconductor nanopillar; and a functional layer covering the conductive layer.

According to a second aspect, a device is provided, comprising: a semiconductor substrate with a planar surface; a semiconductor nanopillar on the semiconductor substrate and substantially perpendicular to the planar surface; an insulating layer covering the semiconductor nanopillar wherein the insulating layer is devoid of an end portion thereof, thus exposing an uninsulated pillar end of the semiconductor nanopillar; and a functional layer covering the insulating layer.

According to a third aspect, a method for fabricating a device is provided, the method comprising: providing a semiconductor substrate with a planar surface; forming at least one semiconductor nanopillar on the semiconductor substrate and substantially perpendicular to the planar surface; covering the semiconductor nanopillar with an insulating layer; depositing a conductive layer on the insulating layer; covering a portion of the conductive layer with a masking layer; removing a conductive layer end of the conductive layer and an insulating layer end of the insulating layer, wherein the conductive layer end and the insulating layer end are not covered by the masking layer, thus exposing an uninsulated pillar end; removing the masking layer; and forming a chemical-attracting layer on the conductive layer, the chemical-attracting layer insulating the conductive layer.

Further embodiments of the present disclosure can be found in the written specification, drawings and claims of the present application. According to some embodiments of the present disclosure, the teachings of the present disclosure provide a sensitive, selective, low-power chemical sensor capable of operating reversibly and in real time to detect and measure concentration for chemical species such as ions and selected dissolved chemical species.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 1A shows an exemplary semiconductor nanopillar (120) on a semiconductor substrate (110) with a planar surface (115)

FIG. 1B shows an exemplary insulating layer (130) covering the semiconductor nanopillar (120) and substrate (110)

FIG. 1C shows an exemplary insulating layer (130) covered semiconductor nanopillar (120) deposited with a conductive layer (140).

FIG. 1D shows an exemplary insulating layer (130) covered nanopillar (120) deposited with the conductive layer (140), wherein the conductive layer (140) is coated with a masking layer (150).

FIG. 1E shows an exemplary insulating layer (130) covered nanopillar (120) deposited with the conductive layer (140) wherein an end portion of the nanopillar (120) is exposed forming an uninsulated pillar end (122).

FIG. 1F shows an exemplary insulating layer (130) covered nanopillar (120) deposited with the conductive layer (140) having the uninsulated pillar end (122), and a functional layer (150) formed over the conductive layer.

DETAILED DESCRIPTION

Figure 1A:
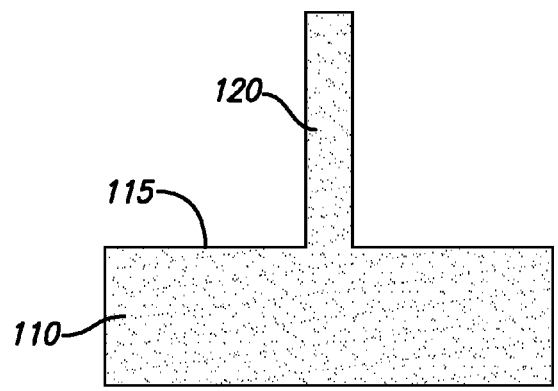
FIGS. 1A-1F show fabrication steps of a device in accordance with an embodiment of the present disclosure. In particular.

In what follows, methods for fabrication of a chemical sensing device are described in accordance with various embodiments of the present disclosure. Nanoscale size pillars can be fabricated by way of example and not of limitation by: performing lithographic or self-assembly methods to form mask followed by etching, use of lithography to pattern catalysts, and bottom-up techniques such as vapor-liquid-solid (VLS) growth. More details regarding fabrication techniques can be found in cross referenced U.S. patent application Ser. No. 12/712,097 for 'Methods for Fabricating High Aspect Ratio Probes and Deforming High Aspect Ratio Nanopillars and Micropillars' and U.S. patent application Ser. No. 12/711, 992 for 'Methods for Fabrication of High Aspect Ratio Micropillars and Nanopillars,' both filed on Feb. 24, 2010, the disclosures of which are incorporated herein by reference in their entirety.

For clarity, the term 'nanoscale' is defined herein to be any structure between 1 nm and 500 nm in width. The term 'pillar' is defined as a substantially upright shaft where the height is much greater than the width, e.g., 5-10 times greater than the width. The term "nanopillar" is defined as nanoscale pillars.

Lithography is a process used in microscale fabrication to enable selective removal for parts of an underlying material by masking portions which should remain. It uses light or electron beam to transfer a geometric pattern from a photo mask to a light-sensitive or electron beam sensitive chemical called a photoresist, coated on the underlying layer. The portion of the photoresist that is exposed to the light or electron beam undergoes a chemical change which causes it to become either soluble or insoluble in the developer solution compared to the unexposed portion depending on the tone of the resist (e.g., positive or negative), thus leaving a mask of the desired pattern on the underlying material. The photoresist can be utilized as a mask directly for removal of exposed underlying material by a removal process such as reactive ion etch or be utilized to pattern a hard mask which can have better resilience in more demanding removal or etching processes.

In accordance with an exemplary embodiment, the applicants utilized an electron-beam type of photoresist to fabricate a patterned aluminum oxide (alumina) hard mask, then removed the electron-beam resist and utilized the patterned alumina hard mask during etching. Lithography and highly anisotropic etching enables a routine fabrication of 30-50 nm nanopillars in silicon with over 40:1 aspect ratios. Transmission and scanning electron microscopy were used to characterize the nanopillars at intermediate points in the process and for the completed pillars.

Subsequent oxidation can further define and enhance the nanopillars. For example, the nanopillars can be further reduced in diameter by a subsequent thermal oxidation, wherein the oxidation process can be designed to self-terminate by oxygen diffusion such that nanopillars below 10 nm in width can be defined with wide processing latitude. Additionally, control of the oxidation process can produce silicon channels which are strained for specific device applications.

Due to the nanometer dimensions and very high surface-to-volume ratios, the conductance of silicon nanopillars can depend strongly on surface chemistry. For example, growing thermal oxide with or without gate metals over a nanopillar creates a structure similar to traditional MOSFETs where charges trapped at the oxide surface change the gate potential which in turn controls the current flowing through the nanopillar core.

By functionalizing the oxide or gate surface, an array of silicon nanopillars can be converted into sensitive, selective, low-power chemical sensors capable of operating reversibly and in real time to detect and measure chemicals such as ions and selected dissolved chemical species. As an example, an oxide surface modified with 3-aminopropyltriethoxysilane can act as a pH sensor, whereas a deposited gold electrode can adsorb hydrogen sulfide and detect H2S concentration. For non-specific ionic concentration, arrays of nanopillars can act as point probes for bulk conductivity measurements, while variably-spaced nanopillars or fins can capacitively sense electric double-layer widths and ionic screening effects without direct electrical connection to the environment.

Devices made from nanopillars are suitable for fabrication within microfluidic channels, with geometries yielding low Reynolds numbers to ensure laminar flow and proper device sensor operation. Features can be added to devices to withstand harsh environment. For example, filter layers may be defined by anisotropic dry etching and hermetically sealed by wafer bonding. With the anisotropic dry etching, it is also possible to build robust filters with small filter openings that can be used to reduce the chance of mechanical damage to the nanopillars by micro-particulates in suspension. By integrating additional features such as one or more on-chip filters, on-chip Pt heaters, or electrolytic pressure generation systems, the device can operate with rapid unload and reload fluid samples. This avoids limiting measurement speed by diffusion of the sample, such as a chemical-containing fluid, to the detector device, and enables the devices of the present disclosure to measure semi-continuously within changing environments FIGS. 1A-1F show steps of fabricating a device for chemical sensing and measurement in accordance with the disclosure. The person skilled in the art will understand that the number of such steps is only indicative and that the process can occur in more or fewer steps according to the various embodiments. For the sake of simplicity, throughout the present disclosure, the term 'pillar' intends to indicate semiconductor nanoscale pillars or nanopillars.

FIG. 1A shows a cross-sectional view of a substantially vertical semiconductor nanopillar (120) on a patterned, or etched semiconductor substrate (110) with a horizontally oriented planar surface (115). By way of example and not of limitation, the substrate (110) and the pillar (120) are made of silicon (Si). The vertical semiconductor nanopillars can also be fabricated on silicon-on-insulator (SOI) instead of bulk silicon substrate, or other semiconductor substrates such as Gallium Arsenide or Germanium.

Figure 1B:
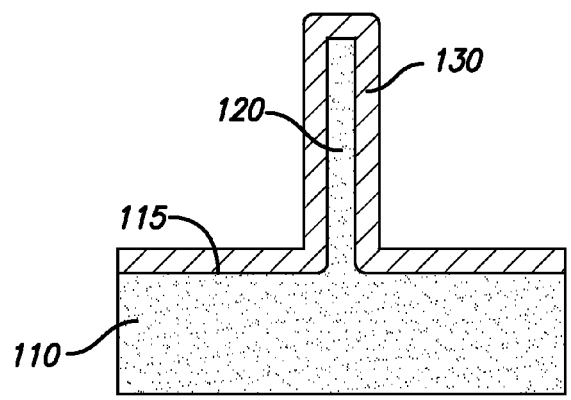

FIG. 1B shows a further cross-sectional view where the substrate (110) and the pillar (120) are covered by an insulating layer (130), e.g., silicon dioxide ($SiO_2$) or other dielectrics. In case the pillar (120) is made of silicon, the insulating layer (130) can be formed by oxidation or vapor phase deposition of silicon and oxygen containing species to form the insulating layer of silicon dioxide.

The terms "cover," and its derivative forms "covered" "covering" and "coverage" are defined herein, for clarity, as completely covering all of the underlying material or materials (e.g., the insulating layer covering the pillar) unless specifically stated as otherwise (e.g., covering portions of or selective coverage).

Figure 1C:
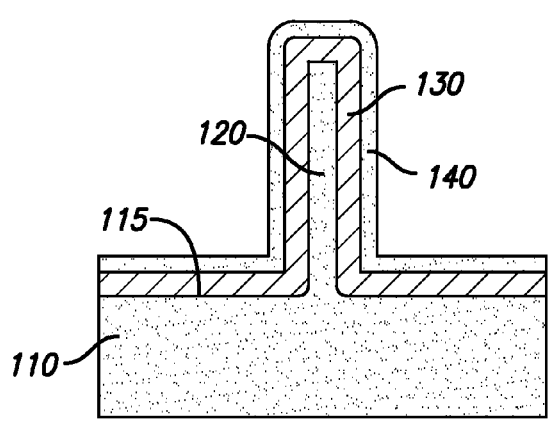

FIG. 1C shows a further cross-sectional view where the insulating layer (130) on the substrate (110) and the pillar (120) is covered by a conductive layer (140) of conductive material e.g., gold (Au) or silver (Ag). According to an embodiment of the disclosure, the conductive material can serve as electrostatic gate on an exterior perimeter and an end of the pillar (120) to modulate the conductivity of the pillar and defines a conductive layer (140)-oxide (130)-semiconductor (120) (e.g., MOS) structure. Such embodiment features a very low threshold voltage (e.g., on the order of 0.5 V) and high on/off ratio with low sub-threshold slopes (e.g., less than 60 mV/decade), as the conductive layer (140) can be deposited to surround the silicon nanopillar (120) on all sides, thereby enabling electrostatic control of a channel. A person skilled in the art of semiconductor fabrication will recognize an opportunity to integrate devices with very high density as a dimension of a conducting channel inside the pillar (120) is nanometers in width.

Figure 1D:
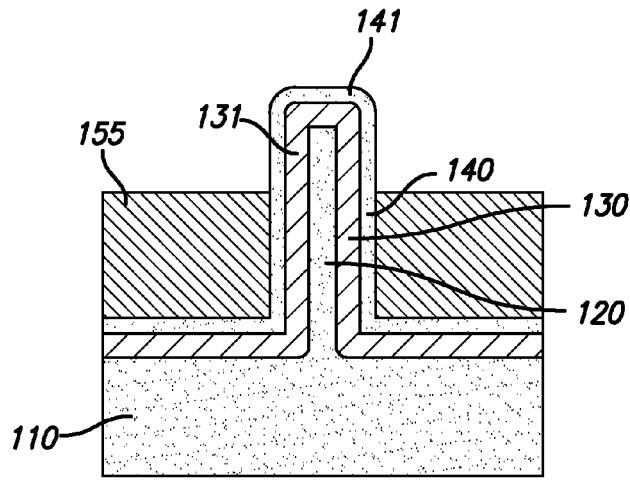

FIG. 1D is a further cross-sectional view where a portion of the conductive layer (140) and the insulating layer (130) on a vertical portion of the pillar (120) is covered by a masking layer (155), which can be a photoresist or a hard mask. The masking layer (155) is patterned so that it covers only selective portions of the pillar. The masking layer (155) protects the covered portions of the conductive layer (140) and the insulating layer (130) to allow selective removal of the conductive layer (140) and the insulating layer (130) in the next step.

Figure 1E:
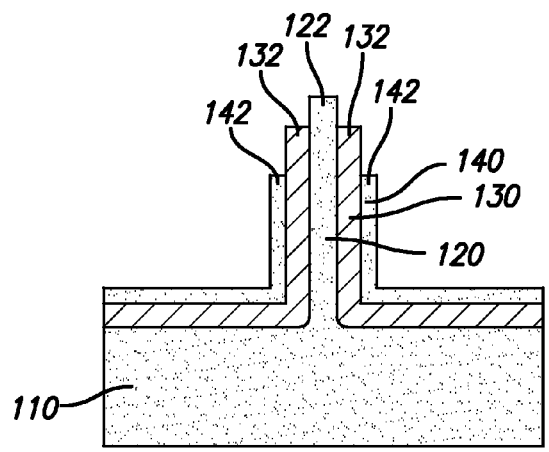

FIG. 1E shows a further cross-sectional view where unprotected portions of the insulating layer (131) and the conductive layer (141) from FIG. 1D are removed from an end portion of the nanopillar (120), for example by a removal process such as etching or chemical-mechanical polishing (CMP). The conductive layer (140) and the insulating layer (130) on a lower portion of the nanopillar (120) and a portion on the substrate (110) are not removed, as the masking layer (155) acts as a cover to protect such portions from the removal process. After the removal process, the masking layer (155) is also removed.

The resulting structure shows, in FIG. 1E an uninsulated pillar end (122) and an insulating layer end (132) protruding beyond a conductive layer end (142). The uninsulated pillar end (122) forms an electrically contactable terminal. The uninsulated pillar end (122), the insulating layer end (132) and the conductive layer end (142) may or may not necessarily terminate at the same location along the pillar. According to an embodiment of the present disclosure, the uninsulated pillar end (122) should terminate at a height equal to or higher than the insulating layer end (132) to ensure contact to the testing fluid. Additionally, the insulating layer end (132) should terminate at a height equal to or higher on the pillar than the conductive layer end (122) to ensure proper insulation between the conductive layer (140) and the electrically contactable terminal formed by the uninsulated pillar end (122). This distinction is for the embodiment of the present disclosure where the gate and the electrically contactable terminal formed by the uninsulated pillar end (122) are not tied together electrically.

Figure 1F:
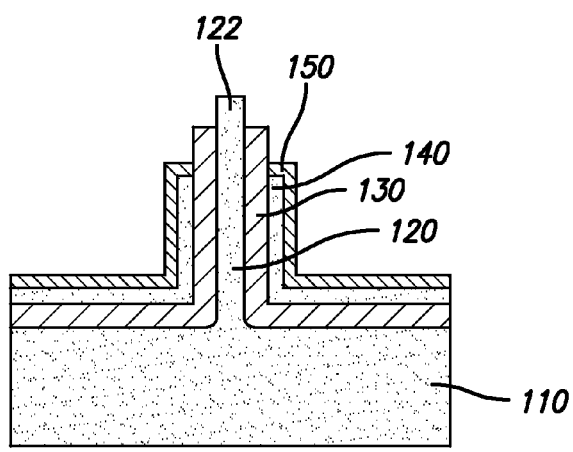

FIG. 1F shows a further cross-sectional view where the conductive layer (140) on the substrate (110) and the pillar (120) are covered by a functional layer (150) which contains one or more chemical species which can attract and hold one or more selected types of chemical species such as ions when a chemical-containing fluid (260) comes in contact to the device. Thus, the functional layer forms a chemically contactable terminal with the conductive layer (140). Therefore, the functional layer (150) can also be known as a chemical-attracting layer (150). The terms "functional layer" (150) and "chemical-attracting layer" (150) are used interchangeably herein.

In an embodiment of the present disclosure, the conductive layer (140) can be optional. The masking layer (155) is used to pattern the insulating layer (130), and the functional layer (150) covers the insulating layer (130). When chemical species, such as ions from the chemical-containing fluid (260) are attracted to and become trapped at the functional layer surface, the chemical species act as gate to the FET.

The chemical-containing fluid (260) may be a gas, a liquid or a suspension. An example of the functional layer (150) can be 3-aminopropyltriethoxysilane, which can attract hydrogen ions. According to an embodiment of the present disclosure, the functional layer (150) can hold ions next to or near the conductive layer (140) and serve to modulate an electrostatic gate formed by the conductive layer (140).

The functional layer (150) can be made of the same material as the conductive layer (140) and can be deposited at the same time. For example, gold material can be used to form a functional layer (150) for attracting $H_2S$ and a conductive layer (140).

Another type of functional layer (150) can have fixed charges (e.g., silicon dioxide, which cab have a partial negative charge on its surface), so that electric double layer formation and ion screening effects can modulate the electrostatic gate terminal formed by the conductive layer (140). The modulation of ionic screening effect on the electrostatic gate can vary as a function of interpillar distance and thus be used to sense specific chemical species such ions and measure ion concentration.

According to various embodiments of the present disclosure and as shown in FIG. 1F, the functional layer (150) covers the conducting layer (140) and can insulate it from the chemical-containing fluid (260). Therefore, the functional layer (150) may physically encompass multiple materials or layer to serve a dual function to attract chemical species and to insulate. For example, for the functional layer (150) containing gold used to attract and sense $H_2S$, the functional layer (150) may be a bilayer comprising an attractive layer (e.g., gold) covered by a semi-permeable layer which allows $H_2S$ to pass through the semi-permeable layer and reach the gold while insulating the underlying conductive layer (140) and/or the attractive layer from the remaining chemical species in the chemical-containing fluid (260). The constituent materials do not have to be physically separated by planar layers. For example, the functional layer (150) may also be an insulating, semi-permeable matrix with domains of gold within.

According to further embodiments of the present disclosure, the gate terminal can be tied to the electrically contactable terminal formed by the uninsulated pillar end (122) and the functional layer (150) may not have to insulate the conductive layer (140).

The formation of the functional layer (150) may be by deposition from solution, sputtering, vapor deposition, or other methods. Coverage of the functional layer (150) on the conductive layer (140) and not on the uninsulated pillar end (122) as shown in FIG. 1F can be provided by a selective deposition process which only deposits on the conducting layer, or by an additional mask and removal process which removes the functional layer (150) from the uninsulated pillar end (122)

According to various embodiments in of the present disclosure, the device can be, but is not limited to, a variety of field-effect transistors (FETs) such as a metal-oxide-semiconductor field-effect transistor (MOSFET) to sense and measure chemical species.

Figure 2:
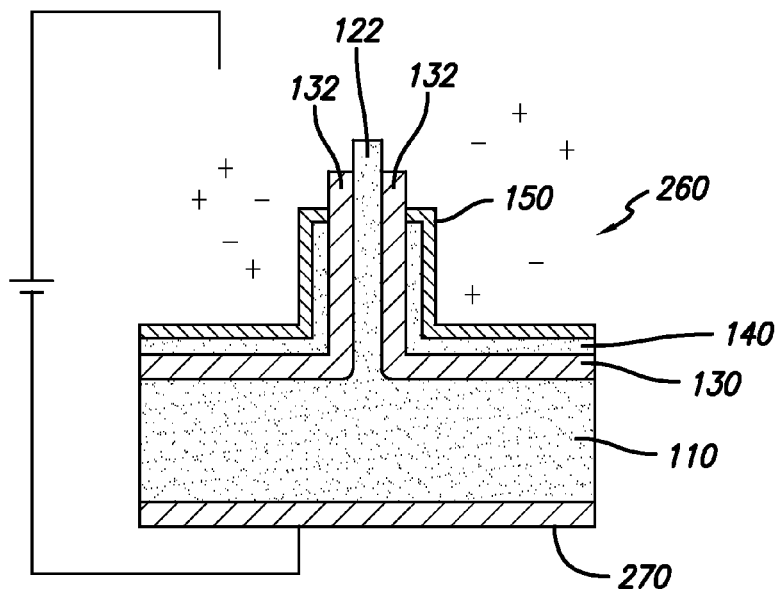
FIG. 2 shows a cross-sectional view of an exemplary chemical sensing device in accordance with a further embodiment of the present disclosure.

FIG. 2 shows a cross-sectional view of an exemplary device in accordance with a further embodiment of the present disclosure for sensing and measuring a chemical concentration of selected species. The substrate (110) and the uninsulated pillar end (122), contacted through a chemical-containing fluid (260) (e.g., an ionic fluid), represent a source and a drain (or vice versa) of the device as a MOSFET for sensing and measuring ion concentration, while conductive layer (140) is the gate of the MOSFET chemical sensing device. The chemical-containing fluid (260) comprise of the selected chemical species and ion, whereby the uninsulated pillar end (122) can be contacted through the chemical-containing fluid (260). However, the ions and the selected chemical species may or may not be the same.

For example as shown in FIG. 2 the uninsulated pillar end (122) can be a current source and electrically contacted through the chemical-containing fluid (260) while the substrate can be a current drain terminal and electrically contacted through a backside contact layer (270). The backside contact layer (270) can also be called a backside terminal. By forming a voltage difference between the source and drain, the current flow from the source to the drain is controlled by charges on or near the conductive layer (140) as the gate terminal.

Upon contacting the device to a chemical-containing fluid (260), the selected chemical species, in the chemical-containing fluid (260), can be attracted by the functional layer (150) and change the amount of total charges on or near the conductive layer (140) gate. The change in total charges on or near the conductive layer (140) gate terminal changes the current flow from source to drain and can be used to sense the presence of ions in the chemical-containing fluid. This would serve to modulate the current flow from the source to the drain. Such configuration of the MOSFET structure, or a plurality thereof, can serve as the chemical sensing device.

For selected chemical species that are non-ionic, the total charge on the gate terminal can changed by the displacement of fixed charges on the functional layer (150). For example in case where the functional layer (150) is gold, the gold surface can have a partial negative charge which can be removed when a selected chemical species such as $H_2S$ is absorbed on the gold surface.

Figure 3:
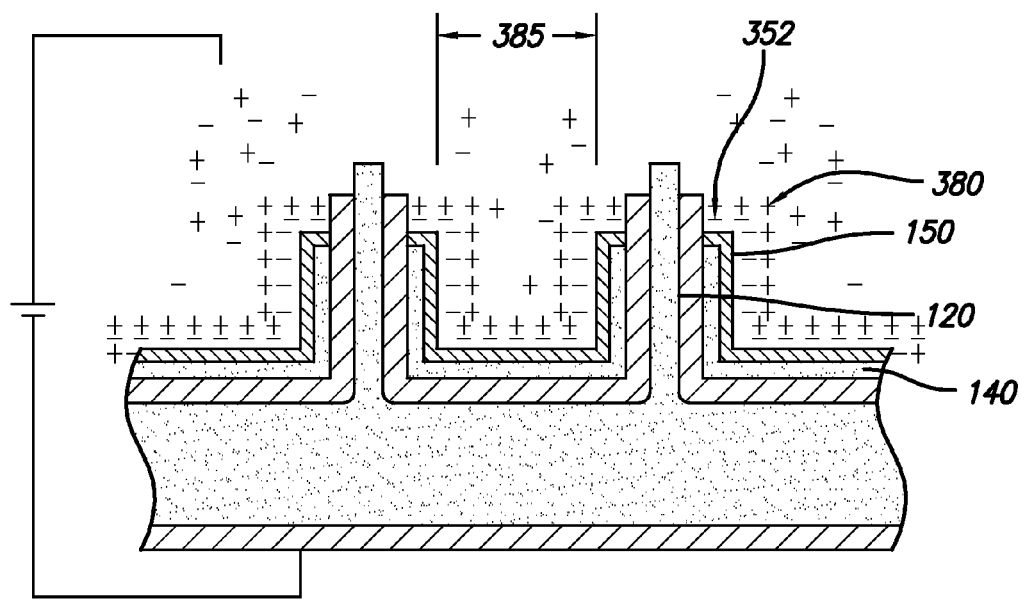
FIG. 3 shows yet another exemplary chemical sensing device in accordance with another embodiment of the present disclosure.

FIG. 3 shows yet another exemplary chemical sensing device in accordance with another embodiment of the present disclosure utilizing the chemical sensing device to measure ion concentration or pH. Shown herein is a plurality of the pillars (120) fixed at an interpillar distance (385). A conductive layer (140) is covered by a functional layer (150) having a plurality of fixed negative charges (352) on its surface.

A chemical-containing fluid (260) surrounding the pillars (120) provides positive ions which forms an electric double layer on each of the pillar (120) due to attraction to the fixed negative charges (352) of the functional layer (150). Positive charges of the electric double layer (380) on each of the pillars (120) can repel the positive charges on the electric double layer (380) on its adjacent pillars (120), and the positive charges in the chemical-containing fluid.

This repulsive force is greater at smaller interpillar distance (385) and can limit the amount of attracted charged ions (in this case positive) from reaching the electric double layer (380). The repulsive force can also be moderated by the screening effect of the free ions in the chemical-containing fluid (260) which shields the repulsive force of those adjacent the electric double layers (380).

Thus, an ion concentration model can be created for the net charge density of the double layer as a function of the interpillar distance (385) and the ion concentration of the chemical-containing fluid (260). By utilizing at least two chemical sensing devices, each with a distinct and known interpillar distance (385), the ion concentration of the chemical-containing fluid (260), can be measured by measuring the source to drain current flow for each of the two devices and comparing the difference in the current flow to the difference between the interpillar distance (385) for the two devices.

Figure 4:
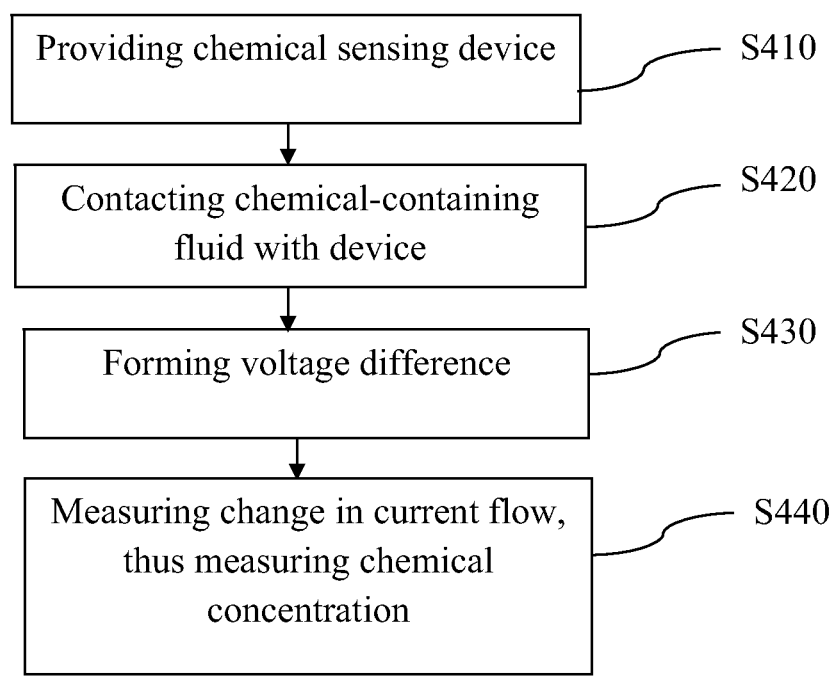
FIG. 4 shows a flow chart for an exemplary method for using the chemical sensing device of the present disclosure for measuring chemical concentration.

FIG. 4 shows a flow chart for an exemplary method for using the chemical sensing device of the present disclosure for measuring chemical concentration. The flow chart shows a method of measuring chemical concentration comprising: 1) providing the chemical sensing device (S410), 2) contacting a chemical-containing fluid (260) with the device such that a selected type of chemical species in the chemical-containing fluid is suitable to be attracted by the functional layer (150) of the device (S420), 3) forming a voltage difference between the uninsulated pillar end (122) and the semiconductor substrate (110) of the device (S430), and 4) measuring a change in current flow between one or more of the uninsulated pillar end (122) and the semiconductor substrate (110) of the device, thus measuring the chemical species concentration (S440). Although this embodiment shows a method comprising of four steps, it is noted that the measurement can be accomplished in more or less steps.

In accordance with various embodiments of the present disclosure, the MOSFET structure has a functional layer (150) which can attract and hold selected chemical species from a chemical-containing fluid (260) next to or near the conducting layer (140) serving as a gate terminal for the MOSFET structure. As the movement of the chemical species in the fluid is in real time and the attraction of the functional layer (150) to selected chemical species can be designed to be reversible, the resulting device can function effectively as a real time, reversible chemical sensor and chemical species measurement device.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

We claim:

1. A device comprising:
a semiconductor substrate with a planar surface;
a semiconductor nanopillar on the semiconductor substrate and substantially perpendicular to the planar surface;
an insulating layer covering the semiconductor nanopillar;
a conductive layer covering the insulating layer, wherein all space between the conductive layer and the semiconductor nanopillar is completely filled by the insulating layer, wherein the conductive layer and the insulating layer are devoid of an end portion thereof, thus exposing an uninsulated pillar end of the semiconductor nanopillar; and
a functional layer covering the conductive layer, wherein an insulating layer end of the insulating layer protrudes beyond a conductive layer end and terminates before the uninsulated pillar end of the semiconductor nanopillar, wherein the functional layer is a bilayer, the bilayer comprising:
an attractive layer for attracting a selected type of chemical species; and
a semi-permeable insulating layer, the semi-permeable insulating layer being on the attractive layer, wherein the semi-permeable insulating layer is configured to allow the selected type of chemical species to pass through and to insulate the attractive layer and the conductive layer of the device.

2. The device of claim 1, wherein the uninsulated pillar end forms an electrically contactable terminal and the functional layer forms a chemically contactable terminal.

3. The device of claim 1, wherein the functional layer is configured to attract a selected type of chemical species.

4. The device of claim 1, wherein the functional layer is configured to attract ions.

5. The device of claim 1, wherein the semiconductor nanopillar and the semiconductor substrate are made of silicon.

6. The device of claim 1, further comprising a conductive backside terminal coated on a backside of the semiconductor substrate, opposite the semiconductor nanopillar.

7. The device of claim 6, the device being a metal-oxide-semiconductor field-effect transistor (MOSFET) structure.

8. The device of claim 7, the conductive layer being a gate terminal of the MOSFET.

9. A microfluidic channel structure comprising one or more devices according to claim 1.

10. The device of claim 1, wherein the semiconductor nanopillar is a plurality of semiconductor nanopillars.

11. The device of claim 8, wherein the semiconductor substrate is a source or a drain of the MOSFET and the uninsulated pillar end is respectively the drain or the source of the MOSFET.

12. The device of claim 1, wherein the attractive layer contains gold.

13. The device of claim 1, wherein the functional layer is an insulating semi-permeable matrix with domain of gold within.

* * * * *